United States Patent [19]
Palermo

[11] Patent Number: 5,636,642
[45] Date of Patent: Jun. 10, 1997

[54] DEFORMABLE TIP SUPER ELASTIC GUIDEWIRE

[75] Inventor: Thomas J. Palermo, Palo Alto, Calif.

[73] Assignee: Target Therapeutics, Inc., Fremont, Calif.

[21] Appl. No.: 428,819

[22] Filed: Apr. 25, 1995

Related U.S. Application Data

[63] Continuation of Ser. No. 62,456, May 11, 1993, Pat. No. 5,409,015.

[51] Int. Cl.$^6$ .................................................. A61B 5/00
[52] U.S. Cl. .................................................. 128/772
[58] Field of Search .................. 128/657, 772; 604/95, 164, 280–282

[56] References Cited

U.S. PATENT DOCUMENTS

| | | |
|---|---|---|
| Re. 33,911 | 5/1992 | Samson et al. . |
| 2,221,138 | 6/1940 | Hendrickson . |
| 2,279,297 | 4/1942 | Bry . |
| 2,905,178 | 9/1959 | Hilzinger, III . |
| 3,338,046 | 8/1967 | Baur et al. . |
| 3,416,531 | 12/1968 | Edwards . |
| 3,452,742 | 7/1969 | Muller . |
| 3,528,406 | 9/1970 | Jeckel et al. . |
| 3,547,103 | 12/1970 | Cook . |
| 3,552,384 | 1/1971 | Pierie et al. . |
| 3,757,768 | 9/1973 | Kline . |
| 3,789,841 | 2/1974 | Antoshkiw . |
| 3,941,119 | 3/1976 | Corrales . |
| 3,973,556 | 8/1976 | Fleischhacker et al. . |
| 4,003,369 | 1/1977 | Heilman et al. . |
| 4,020,829 | 5/1977 | Willson et al. . |
| 4,178,810 | 12/1979 | Takahashi . |
| 4,215,703 | 8/1980 | Willson . |
| 4,430,083 | 2/1984 | Ganz et al. . |
| 4,538,622 | 9/1985 | Samson et al. . |
| 4,545,390 | 10/1985 | Leary ........................ 128/772 |
| 4,554,929 | 11/1985 | Samsom et al. . |
| 4,619,274 | 10/1986 | Morrison ..................... 128/772 |
| 4,665,906 | 5/1987 | Jervis ........................ 128/92 YN |
| 4,721,117 | 1/1988 | Mar et al. . |
| 4,770,188 | 9/1988 | Chikama . |
| 4,846,186 | 7/1989 | Box et al. . |
| 4,925,445 | 5/1990 | Sakamoto et al. . |
| 4,934,380 | 6/1990 | de Toledo . |
| 4,966,163 | 10/1990 | Kraus et al. . |
| 4,969,890 | 11/1990 | Sugita et al. .................. 606/192 |
| 4,971,490 | 11/1990 | Hawkins . |
| 4,984,581 | 1/1991 | Stice . |
| 4,991,602 | 2/1991 | Amplatz et al. . |
| 4,998,923 | 3/1991 | Samson et al. . |
| 5,042,985 | 8/1991 | Elliott et al. . |
| 5,050,606 | 9/1991 | Tremulis . |
| 5,069,226 | 12/1991 | Yamauchi . |
| 5,095,915 | 3/1992 | Engelson . |
| 5,111,829 | 5/1992 | Alvarez de Toledo . |
| 5,120,308 | 6/1992 | Hess . |
| 5,129,890 | 7/1992 | Bates et al. . |
| 5,143,085 | 9/1992 | Wilson et al. . |
| 5,144,959 | 9/1992 | Gambale et al. . |
| 5,171,383 | 12/1992 | Sagaye et al. . |
| 5,213,111 | 5/1993 | Cook et al. . |
| 5,230,348 | 7/1993 | Ishibe et al. . |
| 5,238,004 | 8/1993 | Sahatjian et al. . |

FOREIGN PATENT DOCUMENTS

| | | |
|---|---|---|
| 0014424 | 8/1980 | European Pat. Off. . |
| 0491349 | 6/1992 | European Pat. Off. . |
| 0515201 | 11/1992 | European Pat. Off. . |
| 0519604 | 12/1992 | European Pat. Off. . |
| WO91/15152 | 10/1991 | WIPO . |

*Primary Examiner*—Max Hindenburg
*Attorney, Agent, or Firm*—Morrison & Foerster

[57] ABSTRACT

This invention is a surgical device. It is a guidewire for use in a catheter and is used for accessing a targeted site within a system of lumen within a patient's body. The guidewire may be of a high elasticity metal alloy, preferably a Ni—Ti alloy, having specified physical parameters, and is especially useful for accessing peripheral or soft tissue targets. The "necked" guidewire tip also forms a specific parameter of the invention.

27 Claims, 3 Drawing Sheets

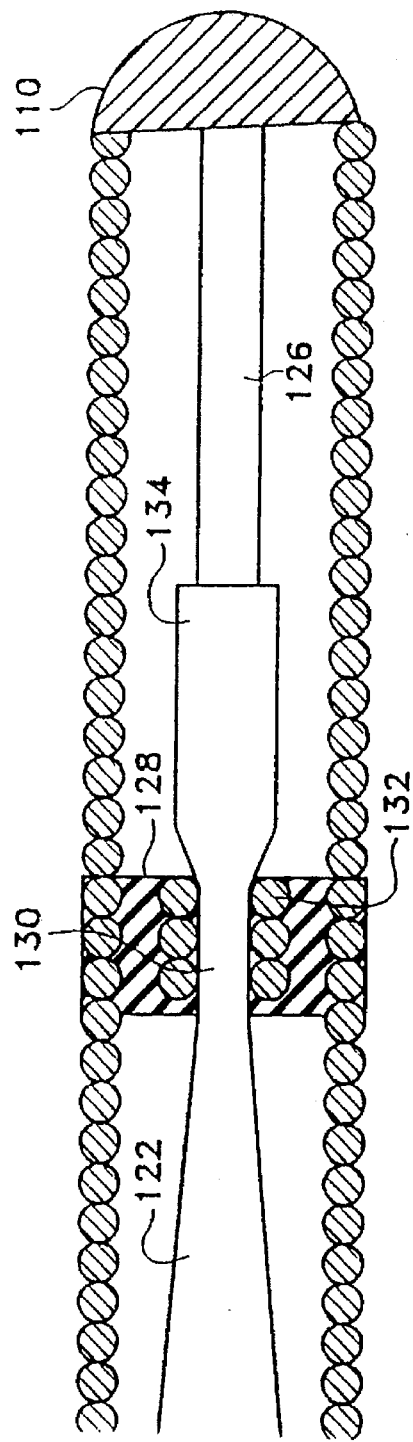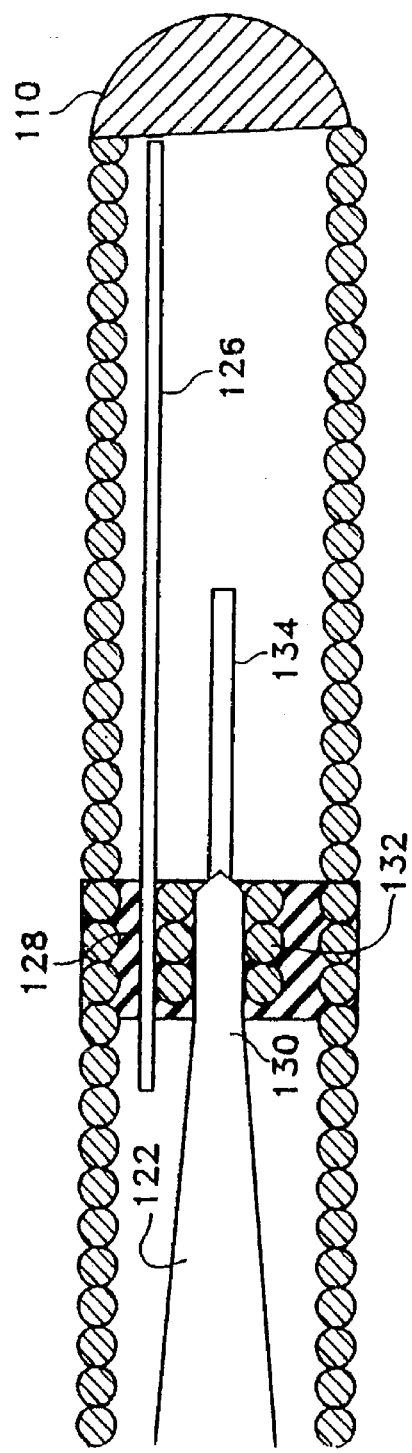

DEFORMABLE TIP SUPER ELASTIC GUIDEWIRE

This is a continuation of U.S. Ser. No. 08/062,456 filed on May 11, 1993, now U.S. Pat. No. 5,409,015, issued on Apr. 25, 1995.

FIELD OF THE INVENTION

This invention is a surgical device. It is a guidewire for use in a catheter and is used for accessing a targeted site in a lumen system of a patient's body. The guidewire may be of a high elasticity metal alloy, preferably a Ni—Ti alloy, having specified physical parameters, and is especially useful for accessing peripheral or soft tissue targets. The "necked" guidewire tip also forms a specific portion of the invention.

BACKGROUND OF THE INVENTION

Catheters are used increasingly as a means for delivering diagnostic and therapeutic agents to internal sites within the human body that can be accessed through the various of the body's lumen systems, particularly through the vasculature. A catheter guidewire is used for guiding the catheter through the bends, loops, and branches forming the blood vessels within the body. One method of using a guidewire to direct the catheter through the torturous paths of these systems of lumen involves the use of a torqueable guidewire which is directed as a unit from a body access point such as the femoral artery to the tissue region containing the target site. The guidewire is typically bent at its distal end, and may be guided by alternately rotating and advancing the guidewire along the small vessel pathway to the desired target. Typically the guidewire and the catheter are advanced by alternately moving the guidewire along a distance in the vessel pathway, holding the guidewire in place, and then advancing the catheter along the axis of the guidewire until it reaches the portion of the guidewire already advanced farther into the human body.

The difficulty in accessing remote body regions such as the body's periphery or the soft tissues within the body, such as the brain and the liver, are apparent. The catheter and its attendant guidewire must be both flexible, to allow the combination to follow the complicated path through the tissue, and yet stiff enough to allow the distal end of the catheter to be manipulated by the physician from the external access site. It is common that the catheter is as long as a meter or more.

The catheter guidewires used in guiding a catheter through the human vasculature have a number of variable flexibility constructions. For instance, U.S. Pat. Nos. 3,789,841; 4,545,390; and 4,619,274 show guidewires in which the distal end section of the wire is tapered along its length to allow great flexibility in that remote region of the guidewire. This is so, since the distal region is where the sharpest turns are encountered. The tapered section of the wire is often enclosed in a wire coil, typically a platinum coil, to increase the column strength of the tapered wire section without significant loss of flexibility in that region and also to increase the radial capacity of the guidewire to allow fine manipulation of the guidewire through the vasculature.

Another effective guidewire design is found in U.S. Pat. No. 5,095,915 which shows a guidewire having at least two sections. The distal portion is encased in an elongated polymer sleeve having axially spaced grooves to allow increased bending flexibility of the sleeve.

Others have suggested the use of guidewires made of various super-elastic alloys in an attempt to achieve some of the noted functional desires.

U.S. Pat. No. 4,925,445, to Sakamoto et al., suggests the use of a two-portion guidewire having a body portion relatively high in rigidity and a distal end portion which is comparatively flexible. At least one portion of the body and the distal end portions is formed of super-elastic metallic materials. Although a number of materials are suggested, including Ni—Ti alloys of 49 to 58% (atm) nickel, the patent expresses a strong preference for Ni—Ti alloys in which the transformation between austenite and martensite is complete at a temperature of 10° C. or below. The reason given is that "for the guidewire to be useable in the human body, it must be in the range of 10° to 20° C. due to anesthesia at a low body temperature." The temperature of the human body is typically about 37° C.

Another document disclosing a guidewire using a metal alloy having the same composition as a Ni—Ti super-elastic alloy is WO91/15152 (to Sahatjian et al. and owned by Boston Scientific Corp.). That disclosure suggests a guidewire made of the precursor to the Ni—Ti elastic alloy. Super-elastic alloys of this type are typically made by drawing an ingot of the precursor alloy while simultaneously heating it. In the unstressed state at room temperature, such super-elastic materials occur in the austenite crystalline phase and, upon application of stress, exhibit stress-induced austenite-martensite crystalline transformations which produce nonlinear elastic behavior. The guidewires described in that published application, on the other hand, are said not to undergo heating during the drawing process. The wires are cold drawn and great pain is taken to assure that the alloy is maintained well below 300° F. during each of the stages of its manufacture. This includes the step of grinding the guidewire to form various of its tapered sections.

U.S. Pat. No. 4,665,906 suggests the use of stress-induced martensite (SIM) alloys as constituents in a variety of different medical devices. Such devices are said to include catheters and cannulas.

U.S. Pat. No. 4,969,890 to Sugita et al., suggests the production of a catheter having a main body fitted with a shape memory alloy member, and having a liquid injection means to supply a warming liquid to allow the shape memory alloy member to recover its original shape upon being warmed by the fluid.

U.S. Pat. No. 4,984,581, to Stice, suggests a guidewire having a core of a shape memory alloy, the guidewire using the two-way memory properties of the alloy to provide both tip-deflecting and rotational movement to the guidewire in response to a controlled thermal stimulus. The controlled thermal stimulus in this instance is provided through application of an RF alternating current. The alloy selected is one that has a transition temperature between 36° C. and 45° C. The temperature 36° C. is chosen because of the temperature of the human body; 45° C. is chosen because operating at higher temperatures could be destructive to body tissue, particularly some body proteins.

U.S. Pat. No. 4,991,602 to Amplatz et al., suggests a flexible guidewire made up of a shape memory alloy such as the nickel-titanium alloy known as nitinol. The guidewire is one having a single diameter throughout its midcourse, is tapered toward each end, and has a bead or ball at each of those ends. The bead or ball is selected to allow ease of movement through the catheter into the vasculature. The guidewire is symmetrical so that a physician cannot make a wrong choice in determining which end of the guidewire to insert into the catheter. The patent suggests that wound wire coils at the guidewire tip are undesirable. The patent further suggests the use of a polymeric coating (PTFE) and an anticoagulant. The patent does not suggest that any particular type of shape memory alloy or particular chemical or physical variations of these alloys are in any manner advantageous.

Another catheter guidewire using Ni—Ti alloys is described in U.S. Pat. No. 5,069,226, to Yamauchi, et al. Yamauchi et al. describes a catheter guidewire using a Ni—Ti alloy which additionally contains some iron, but is typically heat-treated at a temperature of about 400° to 500° C. so as to provide an end section which exhibits pseudo-elasticity at a temperature of about 37° C. and plasticity at a temperature at a temperature below about 80° C. A variation is that only the end portion is plastic at the temperatures below 80° C.

U.S. Pat. No. 5,171,383, to Sagae, et al., shows a guidewire produced from a super-elastic alloy which is then subjected to a heat treatment such that the flexibility is sequentially increased from its proximal portion to its distal end portions. A thermoplastic coating or coil spring may be placed on the distal portion of the wire material. Generally speaking, the proximal end portion of the guidewire maintains a comparatively high rigidity and the most distal end portion is very flexible. The proximal end section is said in the claims to have a yield stress of approximately five to seven $kg/mm^2$ and an intermediate portion of the guidewire is shown in the claims to have a yield stress of approximately 11 to 12 $kg/mm^2$.

Published European Patent Application 0,515,201-A1 also discloses a guidewire produced at least in part of a superelastic alloy. The publication describes a guidewire in which the most distal portion can be bent or curved into a desired shape by a physician immediately prior to use in a surgical procedure. Proximal of the guide tip, the guidewire is of a superelastic alloy. Although nickel-titanium alloys are said to be most desirable of the class shown in that disclosure, no particular physical description of those alloys is disclosed to be any more desirable than another.

Published European Patent Application 0,519,604-A2 similarly discloses a guidewire which may be produced from a superelastic material such as nitinol. The guidewire core is coated with a plastic jacket, a portion of which may be hydrophilic and a portion of which is not.

Examples of Ni—Ti alloys are disclosed in U.S. Pat. Nos. 3,174,851; 3,351,463; and 3,753,700.

None of these disclosures suggest the guidewire composition or configuration described below.

SUMMARY OF THE INVENTION

This invention is a guidewire, preferably a guidewire suitable for introduction into the vasculature of the brain, and a method for its use. The guidewire may be of a super-elastic alloy which preferably is a Ni—Ti alloy having specific physical characteristics, e.g., a stress-strain plateau about 75±10 ksi and another at 25±7.5 ksi (each measured at 3% strain) when the stress-strain relationship is measured to a strain of 6%.

The inventive guidewire is a long wire having a proximal section, an intermediate section, and a distal end section. The guidewire further may have an eccentricity ratio of $1\pm10^{-4}$. The distal end section is typically the most flexible of the sections and is at least about three centimeters long. Desirably, the flexible distal end section is partially tapered and is covered by a coil assembly which is connected to the distal end of the guidewire at its distal tip. The coil assembly may be attached to the distal tip by soldering, preferably after plating or coating the distal end section with a malleable metal. The guidewire assembly may be coated with a polymer or other material to enhance its ability to traverse the lumen of the catheter. Ideally there will be a number of radiopaque markers placed upon the guidewire, e.g., at its distal tip and potentially along the length of the intermediate section to enhance its radiopacity and its ability to transmit torque from the proximal end to the distal end while maintaining a desired flexibility.

A specific variation of the inventive guidewire includes a distal guidewire section having a "neck" or portion of smaller diameter surrounded by areas of larger diameter thereby allowing secure soldering of a ribbon or wire within a coil assembly which extends beyond the guidewire core distal end. The enclosed ribbon or wire may be bent or shaped prior to insertion of the guidewire into the catheter to facilitate movement of the guidewire through turns in the vasculature.

This invention also includes a catheter apparatus made up of the guidewire and a thin-walled catheter designed to be advanced along the guidewire through the vasculature for positioning at a desired site.

BRIEF DESCRIPTION OF THE DRAWINGS

FIG. 4A is a partial cutaway side view of a third embodiment of the distal tip of the FIG. 1 device.

FIG. 4B is a partial cutaway top view of the embodiment shown in FIG. 4A.

DESCRIPTION OF THE INVENTION

Figure 1:
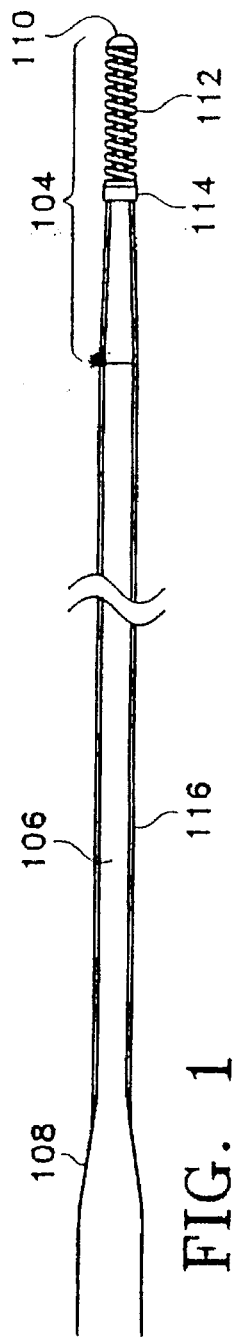
FIG. 1 shows a schematic side view (not to scale) of the major components of the inventive guidewire.

FIG. 1 shows an enlarged side view of a guidewire made according to a very desirable variation of the inventive guidewire (100). The guidewire (100) is made up of the wire core formed of a flexible torqueable wire filament material, of the alloys described below, and has a total length typically about 50 and 300 centimeters. The proximal section (102) preferably has a uniform diameter (along its length) of about 0.010 to 0.025 inches, preferably 0.010 to 0.018 inches. The relatively more flexible distal section (104) extends for 3 to 30 centimeters or more of the distal end of the guidewire (100). There may be a middle section (106) having a diameter intermediate between the diameter of the two portions of the wire adjoining the middle section. The middle section (106) may be continuously tapered, may have a number of tapered sections or sections of differing diameters, or may be of a uniform diameter along its length. If middle section (106) is of a generally uniform diameter, the guidewire core will neck down as is seen at (108). The distal section (104) of the guidewire (100) typically has an end cap (110), a fine wire coil (112), and a solder joint (114). The fine wire coil (112) may be radiopaque and made from materials including but not limited to platinum and its alloys. Specific inventive variations of the distal section (104) are described below. The end cap (110) may be radiopaque to allow knowledge of the position of the coil (112) during the process of inserting the catheter and traversal of the guidewire through the vasculature. All or part of the guidewire proximal section (102) and middle section (106) may be coated with a thin layer of polymeric material to improve its lubricity without adversely affecting the flexibility or shapeability of the guidewire. Such materials include but otherwise are not limited to TEFLON, polyolefins such as polyethylene, polypropylene, or polyurethane.

Other desirable coating polymers including those made from monomers such as ethylene oxide; 2-vinyl pyridine; N-vinylpyrrolidone; polyethylene glycol acrylates such as mono-alkoxy polyethylene glycol mono(meth) acrylates, including mono-methoxy triethylene glycol mono (meth) acrylate, mono-methoxy tetraethylene glycol mono (meth) acrylate, polyethylene glycol mono (meth) acrylate; other hydrophilic acrylates such as 2-hydroxyethylmethacrylate, glycerylmethacrylate; acrylic acid and its salts; acrylamide and acrylonitrile; acrylamidomethylpropane sulfonic acid and its salts cellulose, cellulose derivatives such as methyl cellulose ethyl cellulose, carboxymethyl cellulose, cyanoethyl cellulose, cellulose acetate, polysaccharides such as amylose, pectin, amylopectin, alginic acid, and cross-linked heparin. These monomers may be formed into homopolymers or block or random copolymers. The use of oligomers of these monomers in coating the guidewire for further polymerization is also an alternative. Preferred precursors include ethylene oxide; 2-vinyl pyridine; N-vinylpyrrolidone and acrylic acid and its salts; acrylamide and acrylonitrile polymerized (with or without substantial crosslinking) into homopolymers, or into random or block copolymers.

Additionally, hydrophobic monomers may be included in the coating polymeric material in an amount up to about 30% by weight of the resulting copolymer so long as the hydrophilic nature of the resulting copolymer is not substantially compromised. Suitable monomers include ethylene, propylene, styrene, styrene derivatives, alkylmethacrylates, vinylchloride, vinylidenechloride, methacrylonitrile, and vinyl acetate. Preferred are ethylene, propylene, styrene, and styrene derivatives.

The polymeric coating may be cross-linked using known techniques, e.g., by light such as ultraviolet light, heat, or ionizing radiation, or by peroxides or azo compounds such as acetyl peroxide, cumyl peroxide, propionyl peroxide, benzoyl peroxide, or the like. A polyfunctional monomer such as divinylbenzene, ethylene glycol dimethacrylate, trimethylolpropane, pentaerythritol di- (or tri- or tetra-) methacrylate, diethylene glycol, or polyethylene glycol dimethacrylate, and similar multifunctional monomers capable of linking the monomers and polymers discussed above.

Preferred are silicone-based compounds, the hydrophilic polymers such as polyvinylpyrrolidone, polyethylene oxide, or polyhydroxyethylmethacrylate or copolymers, or mixtures, or blends thereof. The polymeric coating (116) is shown in FIGS. 1, 2 and 3.

Figure 2:
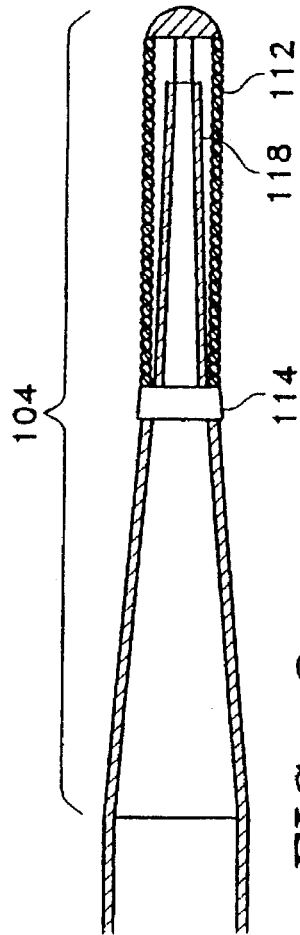
FIG. 2 is a partial cutaway side view of one embodiment of the distal tip of the FIG. 1 device.

FIG. 2 shows a partial cutaway of one embodiment of the distal section (104) and the distal end of the intermediate section (106). The metallic guidewire core is shown partially coated with polymer (116) and a malleable metal coating (118) on the tapered portion of the distal tip. The malleable metal may be selected from suitable radiopaque materials such as gold or other easily solderable materials such as silver, platinum, palladium, rhodium, and alloys of the above. The tip also includes a radiopaque coil (112) which is bounded on its proximal end by a solder joint (114) and is joined with the end of the guidewire at (110). The radiopaque coil (112) may be made of known suitable materials such as platinum, palladium, rhodium, silver, gold, and their alloys. Preferred is an alloy containing platinum and a small amount of tungsten. The proximal and distal ends of coil (112) may be secured to the core wire by soldering.

Figure 3:
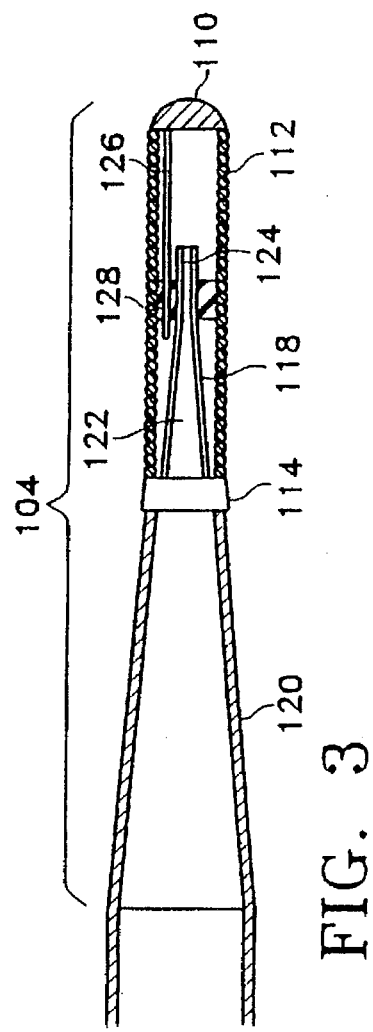
FIG. 3 is a partial cutaway side view of a second embodiment of the distal tip of the FIG. 1 device.

FIG. 3 shows a partial cutaway of another embodiment of the distal section (104) of the inventive guidewire. In this embodiment, the metal guidewire core has a proximal tapered portion (120), a distal tapered section (122) with a solder joint (114) separating the two sections, and a constant diameter tip (124). The distal tip (124) may have constant diameter typically between about 0.002 and 0.005 inches, preferably about 0.003 inches. The distal tip (124) is preferably between about 1 and 5 cm in length, preferably about 2 cm but the portion of constant diameter extends for at least about 25% of the distance between the solder joint (128) and the solder joint (114). This constant diameter section marginally stiffens the distal tip assembly for enhanced control. The entire distal section (104) desirably is between about 20 and 50 cm, preferably about 25 cm in length. The maximum diameter of the proximal tapered portion (120) of the guidewire core typically is between about 0.005 and 0.020 inches, preferably about 0.010 inches. The distal tapered portion (122) and distal tip (124) are again shown with a malleable metal coating (118) such that the distal tapered portion (122) and distal tip (124) stay bent upon forming by the physician. In this embodiment, the fine wire coil (112) is bounded on its proximal end by a solder joint (114) and on its distal end by an end cap (110). The end cap (110) is connected to the guidewire by means of a metallic ribbon (126). The ribbon (126) may be made of stainless steel, platinum, palladium, rhodium, silver, gold, and their alloys or other materials which are plastic and that are easily soldered. The ribbon (126) is soldered to the fine wire coil (112) and to the distal tip (124) of the distal section (104) of the guidewire at a solder joint (128) such that the end cap (110) is secured against the fine wire coil (112).

FIGS. 4A and 4B show yet another inventive embodiment of the distal section (104) of the guidewire (100). FIG. 4A shows a side view, partial cutaway of the inventive guidewire. The fine wire coil (112) may be bounded by a polymer adhesive (136) that joins the coil (112) to the core wire and an end cap (110) and further secured to the guidewire core by a solder joint (128). In this embodiment, the distal section (104) of the guidewire again comprises a tapered portion (120) that is proximal to the polymer adhesive (136) and a tapered portion (122) that is distal to the polymer adhesive (136). The distal section (104) also comprises a smaller diameter portion (130) or "neck" that may be surrounded by optional inner coil (132). The inner coil (132) may be made of a suitable metallic material preferably that is easy to solder and preferably radiopague. It is preferably platinum or stainless steel. One way to produce neck (130) is to flatten the distal portion of the guidewire (134) distal to the neck so that the resulting spade (134) is no longer of circular cross-section but rather is of rectangular shape. This may be more easily visualized in FIG. 4B that shows a cutaway top view of the guidewire shown in FIG. 4A. As in above-described embodiments, the end cap (110) is secured to the guidewire by a metallic ribbon (126). The solder joint (128) secures the guidewire core to the inner helical coil (132) which secures the end cap (110) via the ribbon (126) and further secures the outer fine wire coil (112). This configuration is especially valuable for use with guidewire materials which are not easily solderable. The solder joint need not adhere to the guidewire and yet the inner coil (132), ribbon (126), and outer fine wire coil (112) all are maintained as a single integral unit and have no chance of slipping proximally or distally on the guidewire assembly.

Although the embodiment described with reference to FIGS. 4A and 4B speaks generally of a guidewire made of a high elasticity alloy, materials for the guidewire and the ribbon such as stainless steel, platinum, palladium, rhodium and the like are suitable with that embodiment.

This guidewire is typically used in a catheter which is made up of an elongate tubular member having proximal and distal ends. The catheter is (again) about 50 to 300 centimeters in length, typically between about 100 and 200 centimeters in length. Often, the catheter tubular member has a relatively stiff proximal section which extends along a major portion of the catheter length and one or more relatively flexible distal sections which provide greater ability of the catheter to track the guidewire through sharp bends and turns encountered as the catheter is advanced through the torturous paths found in the vasculature. The construction of a suitable catheter assembly having differential flexibility along its length is described in U.S. Pat. No. 4,739,768.

We have found that certain alloys, particularly Ni—Ti alloys, retain their super-elastic properties during traversal through the vasculature and yet are sufficiently pliable that they provide the physician using the guidewire with enhanced "feel" or feedback and yet do not "whip" during use. That is to say, as a guidewire is turned it stores energy during as a twist and releases it precipitously as it "whips" to quickly recover the stored stress. The preferred alloys do not incur significant unrecovered strain during use. We have also found that if the eccentricity of the wire, i.e., the deviation of the cross-section of the guidewire from "roundness" (particularly in the middle section) is maintained at a very low value, the guidewire is much easier to steer or direct through the vasculature.

The material used in the guidewires of this invention are of shape memory alloys which exhibit super-elastic/pseudoelastic shape recovery characteristics. These alloys are known. See, for instance, U.S. Pat. Nos. 3,174,851 and 3,351,463 as well as 3,753,700; however, the '700 patent describes a less desirable material because of the higher modulus due to an increased iron content. These metals are characterized by their ability to be transformed from an austenitic crystal structure to a stress-induced martensitic (SIM) structure at certain temperatures, and return elastically to the austenitic shape when the stress is removed. These alternating crystalline structures provide the alloy with its super-elastic properties. One such well-known alloy, nitinol, is a nickel-titanium alloy. It is readily commercially available and undergoes the austenite-SIM-austenite transformation at a variety of temperature ranges between −20° C. and 30° C.

These alloys are especially suitable because of their capacity to elastically recover almost completely to the initial configuration once the stress is removed. Typically there is little plastic deformation, even at relatively high strains. This allows the guidewire to undertake substantial bends as it passes through the body's vasculature, and yet return to its original shape once the bend has been traversed without retaining any hint of a kink or a bend. However, the tips shown are sufficiently plastic that the initial tip formation is retained. Nevertheless, compared to similar stainless steel guidewires, less force need be exerted against the interior walls of the vessels to deform the guidewire of the invention along the desired path through the blood vessel thereby decreasing trauma to the interior of the blood vessel.

A guidewire, during its passage through the vasculature to its target site, may undertake numerous bends and loops. The desirably of enhancing the ease with which a guidewire may be twisted to allow the bent distal tip to enter a desired branch of the vasculature cannot be overstated. We have found that a major factor in enhancing such ease of use, that is, in enhancing the controllability of the guidewires is by controlling the eccentricity of the cross-section of the middle portion of the guidewire. We have found that by maintaining the middle portion of the guidewire (106 in FIG. 1) to an eccentricity ratio of $1\pm10^{-4}$, the guidewire is significantly more controllable than those which fall outside this ratio. By "eccentricity", we mean that at any point along the guidewire the the ratio of the largest diameter at that cross-section to the smallest diameter of the wire at that cross-section.

To achieve these results of high strength and enhanced control even while allowing feedback to the attending physician during use, we have found that the following physical parameters of the alloy are important. In a stress-strain test as shown on a stress-strain diagram such as that found in FIG. 5, the stress found at the midpoint of the upper plateau (UP) (measured, e.g. at about 3% strain when the test end point is about 6% strain) should be in the range of 75 ksi (thousand pounds per square inch)±10 ksi and, preferably, in the range of 75 ksi±5 ksi. Additionally, this material should exhibit a lower plateau (LP) of 25±7.5 ksi, preferably 20±2.5 ksi, measured at the midpoint of the lower plateau. The material preferably has no more than about 0.25% residual strain (RS) (when stressed to 6% strain and allowed to return) and preferably no more than about. 0.15% residual strain.

The preferred material is nominally 50.6%±0.2% Ni and the remainder Ti. The alloy should contain no more than about 500 parts per million of any of O, C, or N. Typically such commercially available materials will be sequentially mixed, cast, formed, and separately co-worked to 30–40%, annealed and stretched.

Figure 5:
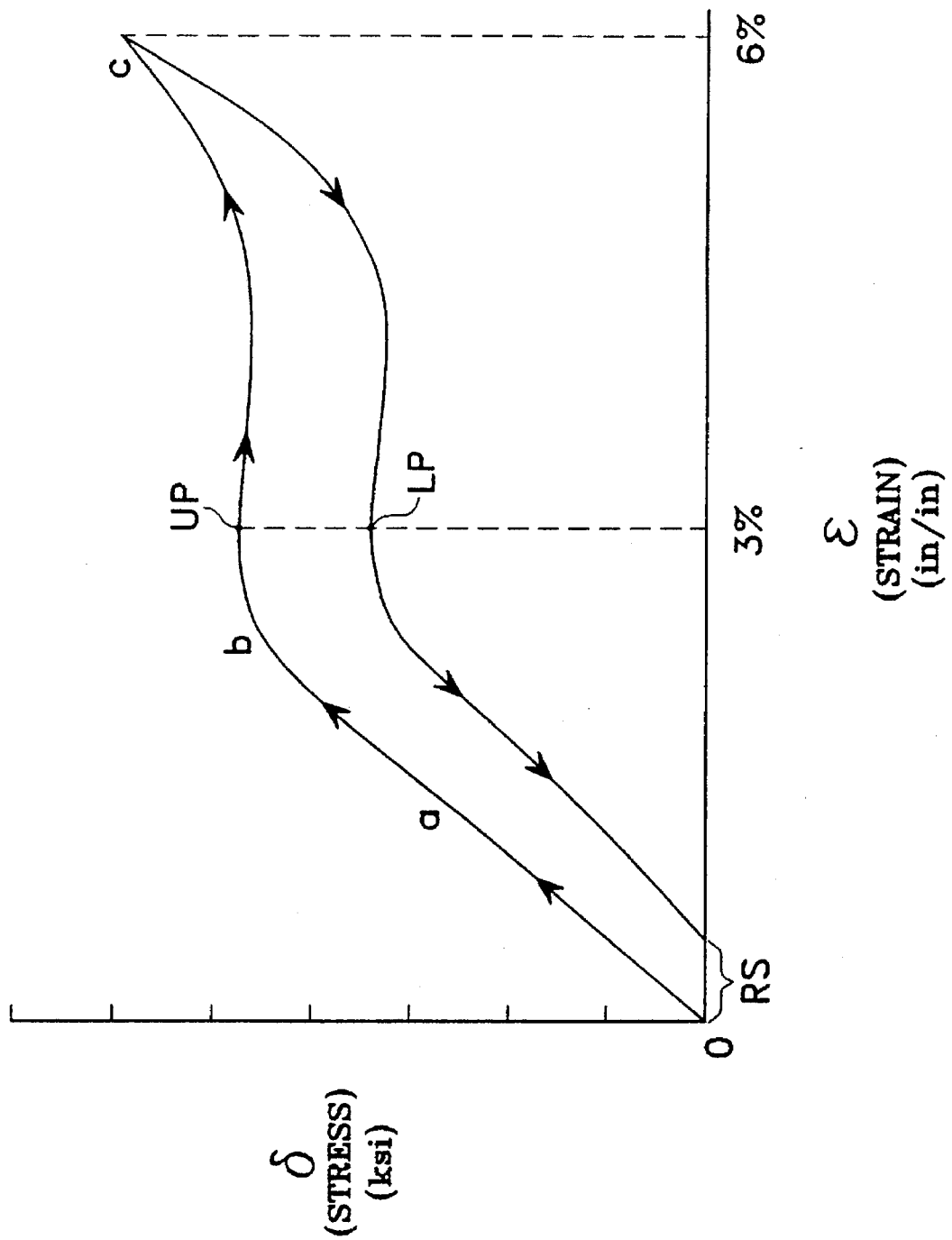
FIG. 5 shows a typical stress-strain diagram for a Ni—Ti alloy displaying objective criteria for selection of alloys for the inventive guidewire.

By way of further explanation, FIG. 5 shows a stylized stress-strain diagram showing the various parameters noted above and their measurement on that diagram. As stress is initially applied to a sample of the material, the strain is at first proportional (a) until the phase change from austentite to martensite begins at (b). At the upper plateau (UP), the energy introduced with the applied stress is stored during the formation of the quasi-stable martensite phase or stress-induced-martensite (SIM). Upon substantial completion of the phase change, the stress-strained relationship again approaches a proportional relationship (at c). The stress is no longer applied when the strain reaches 6%. The measured value (UP) is found at the midpoint between zero and 6% strain, i.e., at 3% strain. If another terminal condition of strain is chosen, e.g., 7%, the measured valued of (UP) and (LP) would be found at 3.5%.

Materials having high UP values produce guidewires which are quite strong and allow exceptional torque transmission but cause a compromise in the resulting "straightness" of the guidewire. We have found that guidewires having high UP values in conjunction with high LP values are not straight. These guidewires are difficult to use because of their tendency to "whip" as they are turned. Again, that is to say, as a guidewire is turned it stores energy during as a twist and releases it quickly. The difficulty of using such a whipping guidewire should be apparent. Materials having UP values as noted above are suitable as guidewires.

Furthermore, materials having values of LP which are high, again, are not straight. Lowering the value of LP compromises the ability of the guidewire to transmit torque but improves the ease with which a straight guidewire may be produced. Lowering the LP value too far, however, results in a guidewire which, although round, has poor tactile response. It feels somewhat "vague" and "soupy" during its use. The LP values provided for above allow excellent torque transmission, straightness, and the valuable tactile response.

The values of residual strain discussed above define a materials which do not kink or otherwise retain a "set" or configuration after stress diring use as a guidewire.

EXAMPLE

In each instance, the following procedure was used in producing the data displayed in the table which follows: commercial Ni—Ti alloy wires having a nominal composition of 50.6% Ni and the remainder Ti, and diameters of 0.13", 0.16", or 0.18" were stressed at room temperature. In each instance, values for transition temperature, PS, UP, and LP were measured. Additionally, several of the noted wires were introduced into a U-shaped Tygon tube and spun to allow qualitative evaluation of the roundness and tactile response of the wires. Comments on that response are also found in the following table.

TABLE

| # | Comparative/Invention (C/I) | UP (ksi) | LP (ksi) | PS (%) | A* T°C. | Qualitative Spin Test |
|---|---|---|---|---|---|---|
| 1[1] | I | 74.48 | 31.45 | 0.06 | −11 | Smooth rotation, good feel |
| 2[2] | I | 76.94 | 18.90 | 0.121 | −8 | Smooth rotation, good feel |
| 3[3] | I | 71.92 | 24.06 | 0.10 | 13.5 | Smooth |
| 4[4] | C | 78.24 | 58.82 | 0.20 | −9 | Very rough turning, whipped |
| 5[5] | C | 63.80 | 13.25 | 0.2 | 12.5 | Smooth turning, mushy feel |
| 6[6] | C | 58.30 | 13.31 | 0.0 | −12 | Turned roughly, mushy feel |
| 7[7] | C | — | — | — | — | Difficult to turn |

[1]Commercially available from U.S. Nitinol, Inc.
[2]Commercially available from Special Metals, Inc.
[3]Commercially available from Shape Metal Alloys, Inc.
[4]Commercially available as a plastic coated 0.13" guidewire from Fuji Terumo, Inc.
[5]Commercially available from ITI.
[6]Commercially available from Metal Tek
[7]Stainless Steel
*Measured at room temperature with no applied stress.

These data describe both guidewires made according to the invention and comparative guidewires. Additionally, they show that guidewire made from a typical stainless steel alloy is very difficult to turn using the qualitative test described above.

Although preferred embodiments of the present invention have been described, it should be understood that various changes, adaptations, and modifications may be made therein without departing from the spirit of the invention and the scope of the claims which follow.

I claim as my invention:

1. A guidewire suitable for guiding a catheter within a body lumen, comprising an elongated, flexible metal wire core of a super-elastic alloy having a UP of 75 ksi±10 ksi and an LP of 25±7.5 ksi measured at 3% strain.

2. The guidewire of claim 1 where the guidewire has a eccentricity ratio of 1±10$^{-4}$.

3. The guidewire of claim 1 having a distal section, a middle section, and a proximal section.

4. The guidewire of claim 1 in which the super-elastic alloy is Ni—Ti.

5. The guidewire of claim 3 in which the at least a portion of the distal portion is covered by an outer coil comprising platinum, tungsten, or an alloy thereof.

6. The guidewire of claim 3 in which the distal section comprises a proximal tapered portion and a constant diameter distal portion.

7. The guidewire of claim 6 wherein an inner coil surrounds the constant diameter distal portion.

8. The guidewire of claim 7 wherein the inner coil comprises a radiopaque metal selected from the group consisting of platinum, tungsten, or an alloy of the two.

9. The guidewire of claim 1 in which at least a portion of the guidewire is coated with a polymeric material.

10. The guidewire of claim 9 where the polymeric material comprises polymers produced from monomers selected from ethylene oxide; 2-vinyl pyridine; N-vinylpyrrolidone; polyethylene glycol acrylates such as mono-alkoxy polyethylene glycol mono(meth) acrylates, including monomethoxy triethylene glycol mono (meth) acrylate, monomethoxy tetraethylene glycol mono (meth) acrylate, polyethylene glycol mono (meth) acrylate; other hydrophilic acrylates such as 2-hydroxyethylmethacrylate, glycerylmethacrylate; acrylic acid and its salts; acrylamide and acrylonitrile; acrylamidomethylpropane sulfonic acid and its salts, cellulose, cellulose derivatives such as methyl cellulose ethyl cellulose, carboxymethyl cellulose, cyanoethyl cellulose, cellulose acetate, polysaccharides such as amylose, pectin, amylopectin, alginic acid, and cross-linked heparin.

11. The guidewire of claim 1 additionally comprising a catheter sheath.

12. A guidewire suitable for guiding a catheter within a body lumen, comprising an elongated, flexible metal wire core of a super-elastic alloy having an LP of 25±7.5 ksi measured at 3% strain and a transition temperature in the range of −11° C. and 13.5° C.

13. The guidewire of claim 12 having a distal section, a middle section, and a proximal section.

14. The guidewire of claim 12 in which the super-elastic alloy is Ni—Ti.

15. The guidewire of claim 12 in which the distal section is tapered to a point.

16. The guidewire of claim 15 in which at least a portion of the distal portion is covered by an outer coil comprising platinum, tungsten, or an alloy thereof.

17. The guidewire of claim 16 in which the outer coil is connected at its distal end by a ribbon joined to the distal portion of the guidewire.

18. The guidewire of claim 12 in which at least a portion of the guidewire is coated with a polymeric material.

19. The guidewire of claim 12 additionally comprising a catheter sheath.

20. A guidewire suitable for guiding a catheter within a body lumen, comprising an elongated, flexible metal wire core of a super-elastic alloy having a UP of 75 ksi±10 ksi and a transition temperature in the range of −11° C. and 13.5° C.

21. The guidewire of claim 20 having a distal section, a middle section, and a proximal section.

22. The guidewire of claim 20 in which the super-elastic alloy is Ni—Ti.

23. The guidewire of claim 20 in which the distal section is tapered to a point.

24. The guidewire of claim 20 in which at least a portion of the distal portion is covered by an outer coil comprising platinum, tungsten, or an alloy thereof.

25. The guidewire of claim 24 in which the outer coil is connected at its distal end by a ribbon joined to the distal portion of the guidewire.

26. The guidewire of claim 20 in which at least a portion of the guidewire is coated with a polymeric material.

27. The guidewire of claim 20 additionally comprising a catheter sheath.

* * * * *